(12) United States Patent
Kim et al.

(10) Patent No.: US 8,493,563 B2
(45) Date of Patent: Jul. 23, 2013

(54) OVERLAY MEASUREMENT APPARATUS AND METHOD

(75) Inventors: Hoyeon Kim, Seoul (KR); Jeongho Yeo, Suwon-si (KR)

(73) Assignee: Samsung Electronics Co., Ltd., Suwon-Si, Gyeonggi-Do (KR)

(*) Notice: Subject to any disclaimer, the term of this patent is extended or adjusted under 35 U.S.C. 154(b) by 175 days.

(21) Appl. No.: 13/208,096

(22) Filed: Aug. 11, 2011

(65) Prior Publication Data

US 2012/0147371 A1 Jun. 14, 2012

(30) Foreign Application Priority Data

Dec. 13, 2010 (KR) ................. 10-2010-0127110

(51) Int. Cl.
*G01B 11/00* (2006.01)
(52) U.S. Cl.
USPC ............................................. 356/400
(58) Field of Classification Search
USPC ................................. 356/399–401
See application file for complete search history.

(56) References Cited

U.S. PATENT DOCUMENTS

| 5,859,439 A * | 1/1999 | Nam et al. .......... 250/548 |
| 2008/0144036 A1 | 6/2008 | Schaar et al. |

FOREIGN PATENT DOCUMENTS

| KR | 10-2000-0043244 | 7/2000 |
| KR | 10-2007-0093186 | 9/2007 |

OTHER PUBLICATIONS

English Abstract for Publication No. 10-2000-0043244.
English Abstract for Publication No. 10-2007-0093186.

* cited by examiner

*Primary Examiner* — Tarifur Chowdhury
*Assistant Examiner* — Abdullahi Nur
(74) *Attorney, Agent, or Firm* — F. Chau & Associates, LLC

(57) ABSTRACT

An overlay measurement apparatus includes a stage on which a wafer comprising first and second overlay measurement keys, which are separated from each other, is placed. A nonlinear medium receives a reference beam and first and second diffracted beams respectively generated by the first and second overlay measurement keys. A detector detects a synthesized beam emitted from the nonlinear medium.

20 Claims, 3 Drawing Sheets

OVERLAY MEASUREMENT APPARATUS AND METHOD

CROSS-REFERENCE TO RELATED APPLICATIONS

This application claims priority to Korean Patent Application No. 10-2010-0127110 filed on Dec. 13, 2010 in the Korean Intellectual Property Office, the disclosure of which is incorporated herein by reference in its entirety.

BACKGROUND

1. Technical Field

The present invention relates to overlay, and more particularly, to an overlay measurement apparatus and a method for performing overlay measurement.

2. Discussion of the Related Art

With the widespread adoption of computers and other electronic information devices, semiconductor devices such as memory storage devices have been developed to provide a high response speed and large storage capacity. Manufacturing technology has been designed to aid in the efficient fabrication of these modern semiconductor devices. This manufacturing technology may be able to fabricate semiconductor devices having a high degree of integration, reliability, fast response speed, etc.

In manufacturing semiconductor devices, providing for a high yield can help to keep manufacturing costs down. A high yield may be provided at least in part by employing an effective apparatus and approach for measuring process errors for one or more process steps that are involved in manufacturing.

In the photolithographic process, misalignment of photoresist patterns formed by exposure and development may be taken into consideration. Accurate alignment is becoming increasingly more difficult to ensure as the alignment margin decreases with the increasing integration density of semiconductor device, for example, as the aperture of a wafer increases and as the number of photolithographic process steps performed increases. Optimization of overlay measurement in checking the alignment of photoresist patterns formed on a wafer may be exploited to minimize or prevent misalignment error.

SUMMARY

In an image-based overlay (IBO) measurement method, center coordinates of a main scale and those of a vernier scale are detected, and the relative difference between the center coordinates of the main scale and the vernier scale is calculated to measure an A diffraction-based overlay (DBO) measurement method uses measurement keys as a main scale and a vernier scale with a slight offset between them. The vernier scale is placed on the main scale. Thus, the main scale and the vernier scale spatially overlap each other. In particular, since the vernier scale is placed on the main scale, the state of the main scale affects the state of the vernier scale. For example, when the main scale has a high step height, coating defects or undercuts may be created in the process of forming the vernier scale. Otherwise, patterns of the vernier scale may be ruined. In this case, the accuracy of the DBO measurement method deteriorates.

Aspects of the present invention provide an overlay measurement apparatus which can measure an overlay in a stable manner.

Aspects of the present invention also provide an overlay measurement method employed to measure an overlay in a stable manner.

However, aspects of the present invention are not restricted to the exemplary embodiments set forth herein.

According to an aspect of the present invention, there is provided an overlay measurement apparatus including a stage on which a wafer is placed. The wafer includes first and second measurement keys which are spaced apart from each other. A reference beam and first and second diffracted beams are respectively generated on a nonlinear medium by the first and second overlay measurement keys. A detector detects a synthesized beam emitted from the nonlinear medium.

According to an aspect of the present invention, there is provided an overlay measurement method including casting a reference beam and first and second diffracted beams generated respectively by first and second overlay measurement keys to a nonlinear medium, and detecting a synthesized beam emitted from the nonlinear medium.

An overlay measurement apparatus includes a stage. A wafer is provided on the stage. The wafer includes a first overlay measurement key generating a first diffracted beam and a second overlay measurement key generating a second diffracted beam. A nonlinear medium receives the first and second diffracted beams and a reference beam and generates a synthesized beam therefrom. A detector detects the synthesized beam generated by the nonlinear medium.

An overlay measurement method includes generating a first diffracted beam using a first overlay measurement key. A second diffracted beam is generated using a second measurement key. The generated first diffracted beam, the generated second diffracted beam, and a reference beam are provided to a nonlinear medium to produce a synthesized beam therefrom. The synthesized beam generated from the nonlinear medium is measured.

A measurement apparatus includes a light source providing a light source beam. One or more beam splitters produce a first, second and third beam from the light source beam. A first overlay measurement key generates a first diffracted beam from the first beam. A second overlay measurement key generates a second diffracted beam from the second beam. A reference grating generates a reference beam from the third beam. A nonlinear medium receives the first and second diffracted beams and the reference beam and generates a synthesized beam therefrom. A photodetector measures the synthesized beam and provides an output signal. A logic circuit creates a measurement based on the output signal provided by the photodetector.

BRIEF DESCRIPTION OF THE DRAWINGS

The above and other aspects and features of the present invention will become more apparent by describing in detail exemplary embodiments thereof with reference to the attached drawings, in which.

DETAILED DESCRIPTION OF THE EMBODIMENTS

Exemplary embodiments of the present invention will now be described more fully hereinafter with reference to the accompanying drawings. This invention may, however, be embodied in different forms and should not be construed as limited to the embodiments set forth herein. The same reference numbers may indicate the same or similar components throughout the specification. In the attached figures, the thickness of layers and regions may be exaggerated for clarity.

It will also be understood that when a layer is referred to as being "on" another layer or substrate, it can be directly on the other layer or substrate, or intervening layers may also be present.

Figure 1:
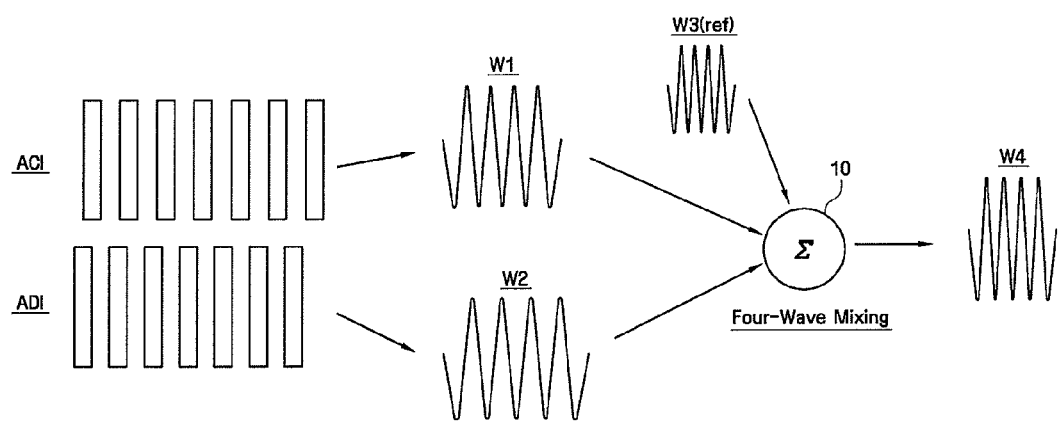
FIG. 1 is a conceptual diagram illustrating an overlay measurement method according to exemplary embodiments of the present invention.
Figure 2:
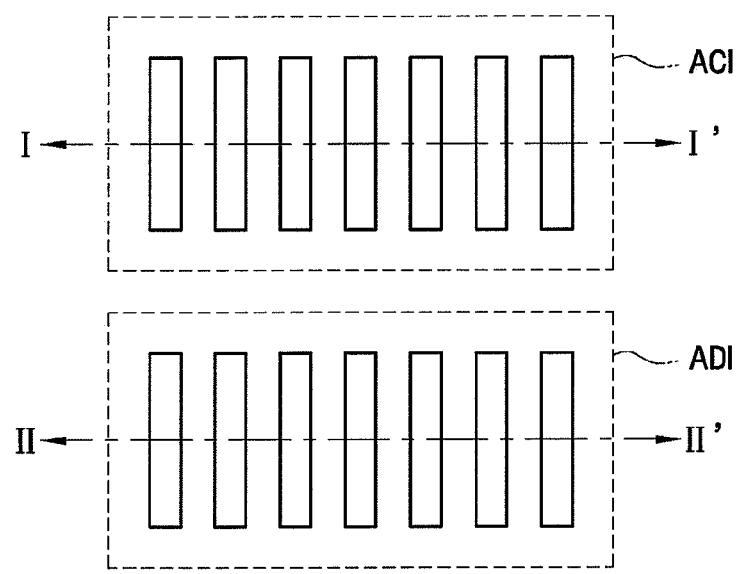
FIG. 2 is a plan view of overlay measurement keys used in an overlay measurement method according to an exemplary embodiment of the present invention.
Figure 3:
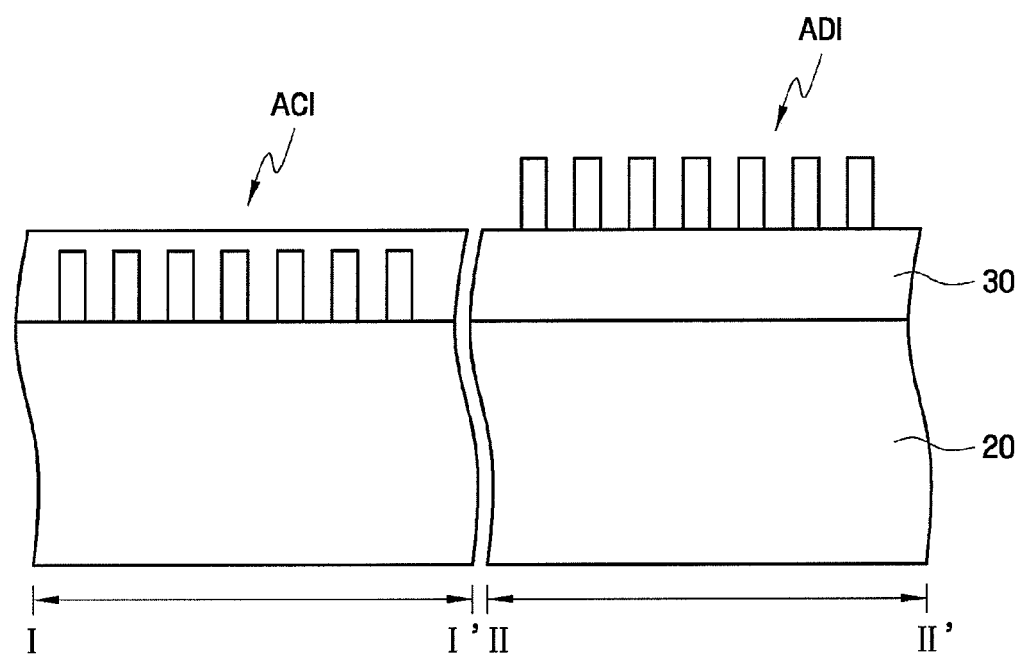
FIG. 3 is a cross-sectional view taken along the lines I-I' and II-II' of FIG. 2.

FIG. 1 is a conceptual diagram illustrating an overlay measurement method according to exemplary embodiments of the present invention. FIG. 2 is a plan view of overlay measurement keys used in an overlay measurement method according to an exemplary embodiment of the present invention. FIG. 3 is a cross-sectional view taken along the lines I-I' and II-II' of FIG. 2.

The overlay measurement may be implemented by providing a sequence of measurement keys. The measurement keys may be used, for example, as markings on a ruler, to provide a system of measurement by which components of the semiconductor device may be accurately measured to ensure for proper alignment. The measurement keys may include a first set of overlay measurement keys and a second set of overlay measurement keys. The first set of overlay measurement keys may be embodied as angle cosign indicators ("ACI") and the second set of overlay measurement keys may be embodied as angle degree indicators ("ADI").

Referring to FIGS. 2 and 3, first and second overlay measurement keys ACI and ADI may be formed in a scribe line region of a wafer 20. Here, the first and second overlay measurement keys ACI and ADI may be separated from each other by a distance. For example, the first and second overlay measurement keys ACI and ADI would not even partially overlap.

In addition, as shown in the drawings, the first and second overlay measurement keys ACI and ADI may be formed in a grating pattern; however, the first and second measurement keys ACI and ADI are not limited to being formed in such a pattern and other patterns are possible.

The two sets of overlay measurement keys ACI and ADI may together be used as a main scale and a vernier scale. A main scale is a scale that provides for a system of measurement that is accurate up to the measure of spacing between the main scale keys. However, the vernier scale may then be used to provide for greater accuracy than the measure of spacing between the scale keys of either scale by taking into account the position in which the keys of the vernier scale match up with the keys of the main scale.

Either of the first and second overlay measurement keys ACI and ADI may be a main scale, for example, the first overlay measurement key ACI may be a main scale. The overlay measurement key that is not used as the main scale may be used as a vernier scale. For example, the second overlay measurement key ADI may be the vernier scale. The first overlay measurement key ACI may be formed, for example, before the second overlay measurement key ADI is formed. The first overlay measurement key ACI may be located, for example, at a lower level than the second overlay measurement key ADI is located at. An insulating layer 30 may be situated between the first overlay measurement key ACI and the second overlay measurement key ADI.

Beams of light cast upon the overlay measurement keys may generate diffraction beams in accordance with the physical arrangement of the sequence of overlay measurement keys.

Referring to FIG. 1, a first diffracted beam W1 is generated by casting a beam of light upon the first overlay measurement key ACI. A second diffracted beam W2 is generated by casting a beam of light upon the second overlay measurement key ADI. The two beams of light used may have identical properties and may be create, for example, by splitting a single beam into two beans. A reference beam W3 is synthesized. Each of the first diffracted beam W1, the second diffracted beam W2, and the reference beam W3 may be directed to a single nonlinear medium 10. The nonlinear medium 10 may then emit a synthesized beam W4 by a wave mixing of the three incident beams. The synthesized beam W4 is analyzed to measure an overlay.

The nonlinear medium 10 generates the synthesized beam W4 using a four-wave mixing (FWM) method. The FWM method is an intermodulation phenomenon in optical systems. In intermodulation, two or more different waves passing through a nonlinear medium are converted into a new wave having frequencies of both the sum of the frequencies of the two or more different waves and the difference between the frequencies of the two or more different waves. Here, if wavelengths of the two or more waves are equal, parametric amplification may occur. The first diffraction beam W1, the second diffraction beam W2, and the reference beam W3 may be generated by splitting a source beam. Accordingly, the three beams may have equal wavelengths. Therefore, the intermodulation of the three beams may result in parametric amplification.

The nonlinear medium 10 may include, for example, bismuth silicon oxide $Bi_{12}SiO_{20}$ (BSO). However, the present invention is not limited thereto, and any material that can produce FWM can be used as the nonlinear medium 10.

In the overlay measurement method according to an exemplary embodiments of the present invention, since the first and second overlay measurement keys ACI and ADI are spatially separated from each other and do not overlap each other, the state of the first overlay measurement key ACI (e.g., a main scale) does not affect the second overlay measurement key ADI (e.g., a vernier scale). Therefore, even when a diffraction-based overlay (DBO) method is used, stable overlay measurement is possible.

Figure 4:
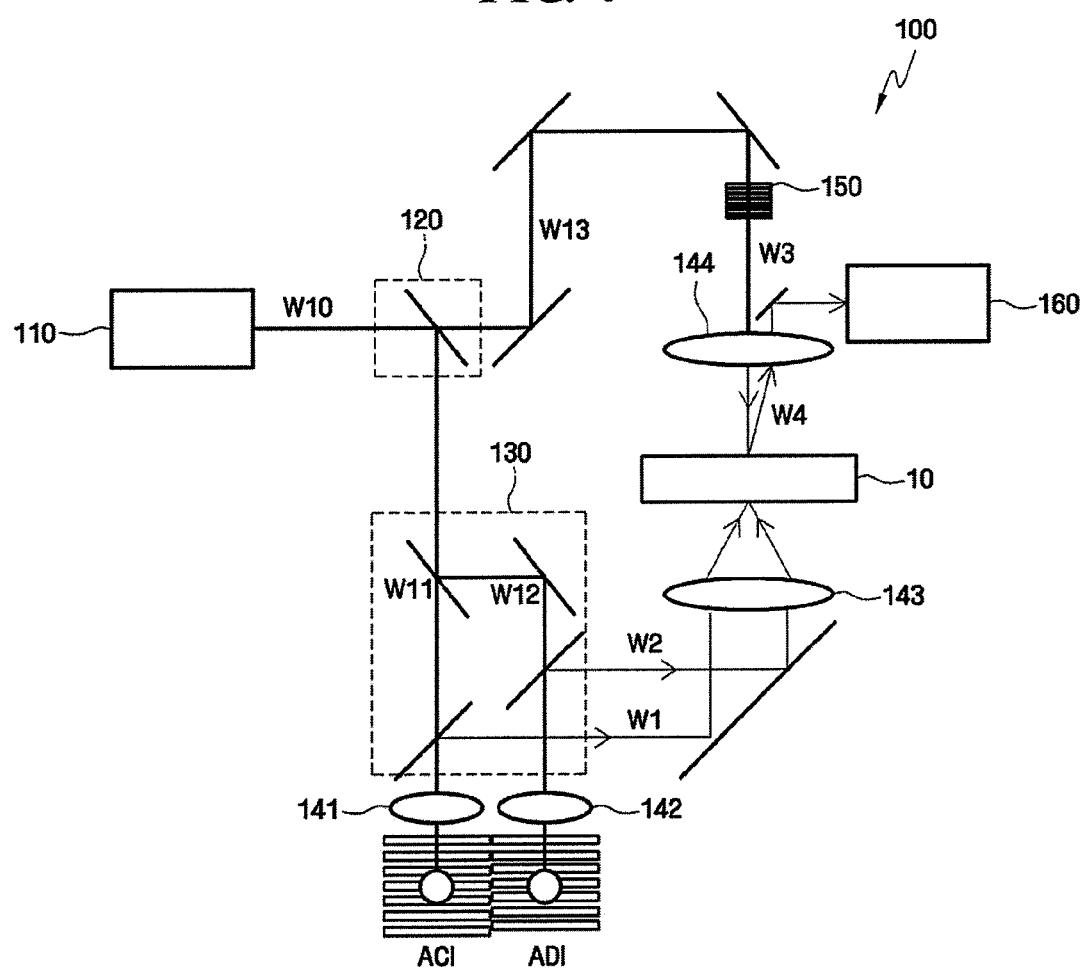
FIG. 4 is a diagram illustrating an overlay measurement apparatus according to exemplary embodiments of the present invention.

FIG. 4 is a diagram illustrating an overlay measurement apparatus 100 according to exemplary embodiments of the present invention.

Referring to FIG. 4, the overlay measurement apparatus 100 according to an exemplary embodiment of the present invention may include a light source 110. The light source 110 may be, for example, a laser. The apparatus 100 may also include first and second beam splitters 120 and 130. The beam splitters 120 and 130 may be, for example, dielectric mirrors or beam splitter cubes. The apparatus 100 may also include first through fourth lenses 141 through 144, a nonlinear medium 10, and a detector 160. As discussed above, the nonlinear medium 10 may be BSO. The detector 160 may be, for example, a photodetector such as a photodiode. In addition, a wafer on which first and second overlay measurement keys ACI and ADI, which are to be measured, are formed may be placed on a stage (not shown).

The light source 110 generates a source beam W10. The source beam W10 may be a monochromatic beam, for example, a laser beam.

The first and second beam splitters 120 and 130 may split the source beam W10 into first through third beams W11 through W13.

The first and second beams W11 and W12 are generated by the first and second beam splitters 120 and 130 and pass through the first and second lenses 141 and 142, respectively, to reach the first and second overlay measurement keys ACI and ADI, respectively. First and second diffracted beams W1 and W2 generated respectively by the first and second overlay measurement keys ACI and ADI are directed to the nonlinear medium 10 through the third lens 143.

The third beam W13 is generated by the first beam splitter 120 and is directed to a reference grating 150. As the third beam W13 passes through the reference grating 150, a reference beam W3 is generated. The reference beam W3 is directed to the nonlinear medium 10 through the fourth lens 144.

The nonlinear medium 10 synthesizes the first and second diffracted beams W1 and W2 and the reference beam W3 using the above-described FWM method and generates a synthesized beam W4. The nonlinear medium 10 may be, for example, $Bi_{12}SiO_{20}$ (BSO). However, the present invention is not limited thereto, and any material that can use the FWM method can be used as the nonlinear medium 10.

The detector 160 detects the synthesized beam W4 to measure an overlay. The detector 160 may provide an output signal based on the detected synthesized beam and the output signal provided by the detector may be used, for example, by a logic circuit, for creating a measurement of the overlay.

It can be understood that the first and second diffracted beams W1 and W2 and the reference beam W3 are generated from one source beam W10. For example, one source beam W10 is split by the first and second beam splitters 120 and 130 to generate the first and second diffracted beams W1 and W2 and the reference beam W3, as described above with respect to FIG. 4.

Each optical path from the light source 110 to the nonlinear medium 10 may have substantially the same length. For example, a first optical path extending from the light source 110 to the first beam splitter 120, through the second beam splitter 130, through the first overlay measurement key ACI to the nonlinear medium 10 that the first diffracted beam W1 reaches, a second optical path extending from the light source 110 to the first beam splitter 120, through the second beam splitter 130, through the second overlay measurement key ADI to the nonlinear medium 10 that the second diffracted beam W2 reaches, and a third optical path extending from the light source 110 to the first beam splitter 120 through the reference grating 150 to the nonlinear medium 10 that the reference beam W3 reaches may have substantially the same length. When the lengths of the optical paths are adjusted as described above, the first and second diffracted beams W1 and W2 and the reference beam W3 can be accurately synthesized by the nonlinear medium 10.

The first and second beams W11 and W12 are directed simultaneously to the first and second overlay measurement keys ACI and ADI, respectively. Since the first and second beams W11 and W12 are analog signals, the first and second diffracted beams W1 and W2 are generated simultaneously only when the first and second beams W11 and W12 are directed simultaneously to the first and second overlay measurement keys ACI and ADI, respectively. When the first and second diffracted beams W1 and W2 are generated simultaneously, they can be accurately synthesized with the reference beam W3 by the nonlinear medium 10.

Those skilled in the art will appreciate that many variations and modifications can be made to the exemplary embodiments without substantially departing from the principles of the present disclosure.

What is claimed is:

1. An overlay measurement apparatus comprising:
   a stage;
   a wafer provided on the stage, the wafer comprising a first overlay measurement key generating a first diffracted beam and a second overlay measurement key generating a second diffracted beam;
   a nonlinear medium receiving the first and second diffracted beams and a reference beam and generating a synthesized beam therefrom; and
   a detector detecting the synthesized beam generated by the nonlinear medium,
   wherein the first and second overlay measurement keys are spatially separated from each other.

2. The apparatus of claim 1, wherein one of the first and second overlay measurement keys is a main scale, and the other one is a vernier scale.

3. The apparatus of claim 1, wherein the reference beam and the first and second diffracted beams are generated from a common source beam.

4. The apparatus of claim 1, further comprising:
   a light source emitting a source beam; and
   a beam splitter splitting the source beam into first through third beams.

5. The apparatus of claim 4, wherein the first and second beams are directed to the first and second overlay measurement keys to generate the first and second diffracted beams, respectively.

6. The apparatus of claim 4, wherein the third beam is directed to a reference grating to form the reference beam.

7. The apparatus of claim 1, wherein the nonlinear medium is bismuth silicon oxide ($Bi_{12}SiO_{20}$).

8. The apparatus of claim 1, wherein the synthesized beam is generated by the nonlinear medium using a four-wave mixing (FWM) method.

9. An overlay measurement method comprising:
   generating a first diffracted beam using a first overlay measurement key;
   generating a second diffracted beam using a second measurement key;
   providing the generated first diffracted beam, the generated second diffracted beam, and a reference beam into a nonlinear medium to produce a synthesized beam therefrom; and
   measuring the synthesized beam generated from the nonlinear medium,
   wherein the first and second overlay measurement keys are spatially separated from each other.

10. The method of claim 9, wherein one of the first and second overlay measurement keys is a main scale, and the other one is a vernier scale.

11. The method of claim 9, wherein the reference beam and the first and second diffracted beams are generated from a common source beam.

12. The method of claim 9, wherein a source beam is split into first through third beams, the first and second beams are directed to the first and second overlay measurement keys to generate the first and second diffracted beams, respectively, and the third beam is directed to a reference grating to form the reference beam.

13. The method of claim 9, wherein the nonlinear medium is bismuth silicon oxide ($Bi_{12}SiO_{20}$).

14. The method of claim 9, wherein the synthesized beam is generated by the nonlinear medium using a four-wave mixing (FWM) method.

15. A measurement apparatus, comprising:
a light source providing a light source beam;
one or more beam splitters producing a first, second and third beam from the light source beam;
a first overlay measurement key generating a first diffracted beam from the first beam;
a second overlay measurement key generating a second diffracted beam from the second beam;
a reference grating generating a reference beam from the third beam;
a nonlinear medium receiving the first and second diffracted beams and the reference beam and generating a synthesized beam therefrom;
a photodetector measuring the synthesized beam and providing an output signal; and
a logic circuit creating a measurement based on the output signal provided by the photodetector,
wherein the first and second overlay measurement keys are spatially separated from each other.

16. The measurement apparatus of claim 15, wherein one of the first overlay measurement key and the second overlay measurement key is a main scale and the other of the first overlay measurement key and the second overlay measurement key is a vernier scale.

17. The measurement apparatus of claim 15, wherein one of the first overlay measurement key and the second overlay measurement key is an angle cosign indicator (ACI) measurement key and the other of the first overlay measurement key and the second overlay measurement key is an angle degree indicator (ADI) measurement key.

18. The measurement apparatus of claim 15, wherein the light source is a laser.

19. The measurement apparatus of claim 15, wherein the nonlinear medium is bismuth silicon oxide ($Bi_{12}SiO_{20}$).

20. The measurement apparatus of claim 15, wherein the measurement created by the logic circuit is an overlay measurement.

* * * * *